United States Patent
Cheon et al.

(10) Patent No.: US 12,324,844 B2
(45) Date of Patent: Jun. 10, 2025

(54) MRI CONTRAST AGENT INCLUDING T1 CONTRAST MATERIAL COATED ON SURFACE OF NANOPARTICLE SUPPORT

(71) Applicant: INVENTERA PHARMACEUTICALS INC., Cheongju-si (KR)

(72) Inventors: Jin Woo Cheon, Seoul (KR); Tae Hyun Shin, Yongin-si (KR)

(73) Assignee: INVENTERA PHARMACEUTICALS INC., Seoul (KR)

( * ) Notice: Subject to any disclaimer, the term of this patent is extended or adjusted under 35 U.S.C. 154(b) by 462 days.

(21) Appl. No.: 17/126,340

(22) Filed: Dec. 18, 2020

(65) Prior Publication Data

US 2021/0113717 A1 Apr. 22, 2021

Related U.S. Application Data (63) Continuation of application No. 14/759,288, filed as application No. PCT/KR2014/000062 on Jan. 3, 2014, now abandoned.

(30) Foreign Application Priority Data

Jan. 4, 2013 (KR) .................. 10-2013-0001002

(51) Int. Cl.
| | | |
|---|---|---|
| A61K 49/18 | (2006.01) | |
| A61K 49/08 | (2006.01) | |
| A61K 49/12 | (2006.01) | |
| A61K 49/14 | (2006.01) | |

(52) U.S. Cl.
CPC .......... *A61K 49/1878* (2013.01); *A61K 49/08* (2013.01); *A61K 49/126* (2013.01); *A61K 49/14* (2013.01)

(58) Field of Classification Search
CPC ............ A61K 49/1863; A61K 49/1878; A61K 2123/00; A61K 49/08; A61K 49/126; A61K 49/14
See application file for complete search history.

(56) References Cited

U.S. PATENT DOCUMENTS

| | | | |
|---|---|---|---|
| 9,040,637 B2 | 5/2015 | Axelsson et al. | |
| 2005/0265922 A1 | 12/2005 | Nie et al. | |
| 2009/0011064 A1 | 4/2009 | Margel | |
| 2009/0110644 A1 | 4/2009 | Margel et al. | |
| 2011/0014296 A1 | 1/2011 | Chen et al. | |
| 2011/0200534 A1* | 8/2011 | Cheon ................ | A61K 49/1836 977/773 |
| 2014/0350193 A1 | 11/2014 | Axelsson et al. | |
| 2016/0000942 A1 | 7/2016 | Cheon et al. | |
| 2018/0361000 A1 | 12/2018 | Weissleder | |
| 2019/0083660 A1 | 3/2019 | Cheon et al. | |

FOREIGN PATENT DOCUMENTS

| | | |
|---|---|---|
| CN | 112089851 | 12/2020 |
| CN | 112807449 | 5/2021 |
| EP | 2942064 | 11/2015 |
| JP | 2014-534277 | 12/2014 |
| KR | 10-2015-0115760 | 10/2005 |
| KR | 10-2007-0058358 | 6/2007 |
| KR | 10-2008-0071463 | 8/2008 |
| KR | 1020090033953 | 4/2009 |
| KR | 1020100023778 | 3/2010 |
| KR | 1020110050213 | 5/2011 |
| WO | WO 99/62079 | 12/1999 |
| WO | WO 2010/048268 | 4/2010 |
| WO | WO 2012/020911 | 2/2012 |
| WO | WO 2014/107055 | 7/2014 |

OTHER PUBLICATIONS

Office Action from Chinese Application No. 202011048294.7, dated May 9, 2022, 13 pages (with machine translation).
Alric, C, et al., "Gadolinium Chelate Coated Gold Nanoparticles As Contrast Agents for Both X-ray Computed Tomography and Magnetic Resonance Imaging", JAGS, pp. 5908-5915 (Year 2008).
Bridot, J., et al., "Hybrid Gadolinium Oxide Nanoparticles: Multimodal Contrast Agents for in Vivo Imaging", J. Am. Chem. Soc. 2007, 129, pp. 5076-5084.
Extended European Search Report from corresponding European Patent Application No. 17753543 2, dated Oct. 7, 2019, 10 pages.
Gole, A., et al.; "Iron Oxide Coated Gold Nanorods: Synthesis, Characterization, and Magnetic Manipulation", Langmuir 2008, 24, pp. 6232-6237.
H.P Erickson et al., "Size and Shape of Protein Molecules at the Nanometer Level Determined by Sedimentation, Gel Filtration, and Electron Microscopy," Biol. Proceed. Online, 2009, 11:32-51.
Hyeon et al., "Development of a contrast agent resonance imaging using nanoparticles," Angew. Chem. Int. Ed., 2007, 46:5397-5.
International Preliminary Report on Patentability in Appln. No. PCT/KR2014/000062, dated Jul. 7, 2015, 10 pages.
International Preliminary Report on Patentability in Appln. No. PCT/KR2017/001852, dated Aug. 21, 2018, 11 pages.
International Search Report (ISR) from corresponding PCT Application No. PCT/KR2017/001852, dated Jun. 13, 2017 and its English translation, 10 pages.
International Search Report and Written Opinion in Appln. No. PCT/KR2014/000062, mailed Apr. 30, 2014, 9 pages.
Lee, J. H., et al.; "Artificially engineered magnetic nanoparticles for Ultra-sensitive molecular imaging", Nature Medicine. vol. 13, No. 1, Jan. 2007, pp. 95-99.

(Continued)

*Primary Examiner* — Michael G. Hartley
*Assistant Examiner* — Leah H Schlientz
(74) *Attorney, Agent, or Firm* — Sughrue Mion, PLLC (57) ABSTRACT

A magnetic resonance imaging (MRI) T1 contrast agent composition including T1 contrast material coated on the surface of a nanoparticle support and an imaging method using the MRI T1 contrast agent. The MRI T1 contrast agent composition has excellent T1 spin magnetic relaxation effects by modifying the paramagnetic T1 contrast material on the nanoparticle support having a certain diameter such that the paramagnetic T1 contrast material has a certain thickness or less, and thereby remarkably increasing the surface-to-volume ratio of the T1 contrast material. The MRI T1 contrast agent provides more precise and clear T1 positive contrast images, and is thus useful for highly reliable image diagnosis.

9 Claims, 2 Drawing Sheets

(56) References Cited

OTHER PUBLICATIONS

Na, H. B., et al.; "Development of a T1 Contrast Agent for Magnetic Resonance Imaging Using MnO Nanoparticles", Angew. Chem. Int. Ed. 2007, 46, pp. 5397-5401.

Office Action from corresponding Japanese Patent Application No. 2018-543635, dated Aug. 26, 2019, 8 pages.

Riviere et al., "Hybrod gadolimium oxide nanoparticles: multimodal contrast agents for vivo imaging," J. Am. Chem. Soc., 2007, 129:5076-5084.

Ryu et al., "Synthesis and Electrochemical Characterization of Silica-Manganese Oxide with a Core-shell Structure and Various Oxidation States," Bulletin of the Korean Chemical Society, 2011, vol. 32, No. 8, pp. 2683-2688.

Shevchenko, E. V., et al.; "Gold/Iron Oxide Core/Hollow-Shell Nanoparticles", Adv. Mater. 2008, 20, pp. 4323-4329.

Yang, H., et al.; "Targeted dual-contrast T1- and T2 weighted magnetic resonance imaging of tumors using multifunctional gadolinium-labeled superparamagnetic iron oxide nanoparticles", Biomaterials 32 (2011) 4584-4593.

Ren et al., "Assembly Behavior of Iron Oxide-Capped Janus Particles in a Magnetic Field", Langmuir, 2012, 28: 1149-1156.

Lee et al., "Super-paramagnetic iron oxide nanoparticles for use in extrapulmonary tuberculosis diagnosis," Clinical Microbiology and Infection, Jun. 1, 2012, 18(6):E149-E157.

Sirlin et al., "Gadolinium-DTPA-dextran: A macromolecular MR blood pool contrast agent1," Academic radiology, Dec. 1, 2004, 11(12):1361-1369.

Ersoy et al., "Biochemical Safety Profiles of Gadolinium-Based Extracellular Contrast Agents and Nephrogenic Systemic Fibrosis," Journal of Magnetic Resonance Imaging, 2007, pp. 1-16.

Sauzedde et al., "Hydrophilic magnetic polymer latexes. 1. Adsorption of magnetic iron oxide nanoparticles onto various cationic latexes," Colloid and Polymer Science, 1999, 277:846-855.

\* cited by examiner

MRI CONTRAST AGENT INCLUDING T1 CONTRAST MATERIAL COATED ON SURFACE OF NANOPARTICLE SUPPORT

CROSS-REFERENCE TO RELATED APPLICATION

This application is a continuation of U.S. application Ser. No. 14/759,288, filed on Jul. 6, 2015, which is a National Stage Application of International Application No. PCT/KR2014/000062, filed on Jan. 3, 2014, which claims priority of Korean Application No. 10-2013-0001002 filed Jan. 4, 2013, the disclosures of which are herein incorporated by reference in their entireties.

TECHNICAL FIELD

The present invention relates to an MRI contrast agent including a T1 contrast material coated on a surface of a support and an imaging method using the MRI contrast agent.

BACKGROUND ART

A nanomaterial exhibits new physical/chemical properties different from those of a bulk material due to the reduced size thereof. As a lot of research of the nanomaterial can control of the composition or shape of the material as well as the size of the material, a nano-region can realize excellent physical/chemical characteristics. Current nanotechnologies have been variously developed, and widely classified into three fields: i) Technology for synthesizing novel ultra-micro-sized substances and materials using a nanomaterial; ii) Technology for manufacturing devices exerting certain functions by combining or arranging nano-sized materials in a nano-device; and iii) Technology in which nanotechnology is grafted into biotechnology (nano-bio).

Of many various nanoparticles, magnetic nanoparticles can be extensively used in the nano-bio technology, such as bio-molecule separation, magnetic resonance imaging (MRI) diagnosis, a magnetic bio-sensor including a giant magnetoresistance sensor, a micro-fluid system, a drug/gene delivery system, and magnetic hyperthermia therapy. In particular, the magnetic nanoparticles can be used as a diagnostic agent for magnetic resonance imaging (MRI). MRI measures nuclear spin relaxation of hydrogen in water molecules, providing T1 and T2 images. MRI contrast agents are classified into a T1 contrast agent and a T2 contrast agent, which serve to amplify T1 or T2 signals. T1 and T2 refer to the spin-lattice relaxation time and the spin-spin relaxation time, after the nuclear spin is excited in MRA, respectively, and produce different contrast effects. The T1 contrast agent is composed of a paramagnetic material capable of causing spin-lattice relaxation. In general, when the T1 contrast agent is present, a bright or positive contrast effect is obtained compared with water. Gd-chelate compounds may be mainly used as a T1 contrast agent, and MAGNEVIS™ (Schering, Germany) used to obtain MRI images is composed of Gd-diethylene triamine pentaacetic acid (Gd-DTPA). Besides, it has been reported that several materials, such as $Gd_2O_3$ (C. Riviere et al. J. Am. Chem. Soc. 2007, 129, 5076.) and MnO (T. Hyeon et al. Angew. Chem. Int. Ed. 2007, 46, 5397.), are used as a T1 contrast agent.

On the contrary, as a T2 contrast agent, superparamagnetic nanoparticles, such as iron oxide nanoparticles, have been mainly used. These magnetic nanoparticles are magnetized by the application of an external magnetic field, generating an induction magnetic field, which influences a spin-spin relaxation process of hydrogen nuclear spins of nearby water molecules, thereby amplifying MRI signals, resulting in a dark or negative contrast effect compared to water. The T2 contrast agent that has been mainly used in the art includes FERIDEX™, RESOVIS™, and COMBIDEX™ that contain an iron oxide component. Recently, magnetism engineered iron oxide (MEIO) having an enhanced contrast effect through substitution of some of iron oxide components has been developed (J. Cheon et al. Nature Medicine 2007, 13, 95).

In MRI, the T1 signal has high signal intensity (bright signal), providing excellent resolution between tissues, thereby discriminating anatomical structures more clearly. In addition, T1 images may characteristically exhibit high signal intensity with respect to sub-acute bleeding (4-14 days after bleeding), and thus are useful to determine the presence or absence of bleeding in a lesion.

Currently, metal chelate-based materials that are generally used as a T1 contrast agent fail to effectively relax the hydrogen nuclear spin in water molecules because of a fast molecule movement (tumbling rate) due to a small size thereof. Meanwhile, metal oxide-based nanoparticles have a slow molecule movement compared with the metal chelate nanoparticles, and allow cooperative nuclear spin relaxation by several metals, but the effect thereof is restricted due to a low surface area-volume ratio. Therefore, the development of T1 MRI contrast agent nanoparticles which have a more efficient contrast effect by overcoming the restriction of the existing T1 contrast agents is required.

Throughout the entire specification, many papers and patent documents are referenced and their citations are represented. The disclosures of cited papers and patent documents are entirely incorporated by reference into the present specification, and the level of the technical field within which the present invention falls and details of the present invention are explained more clearly.

DETAILED DESCRIPTION OF THE INVENTION

Technical Problem

The present inventors have endeavored to develop a contrast agent composition which exerts an excellent T1 MRI contrast effect by effectively inducing spin-lattice relaxation of hydrogen in the water molecule. As a result, the present inventors have found that, in cases where a paramagnetic T1 contrast material is coated on a nanoparticle support having a predetermined diameter such that the paramagnetic T1 contrast material has a predetermined thickness or less, the surface-to-volume ratio of the T1 contrast material increases, and thus the paramagnetic T1 contrast material has a significantly improved T1 magnetic spin relaxation effect (r1, $mM^{-1}s^{-1}$) regardless of the molecular size of the contrast material, and thus have completed the present invention.

Therefore, the present invention has been made in view of the above-mentioned problems, and an aspect of the present invention is to provide a magnetic resonance imaging (MRI) T1 contrast agent composition containing a T1 contrast material coated on a surface of a nanoparticle support.

Other purposes and advantages of the present disclosure will become more obvious with the following detailed description of the invention, claims, and drawings.

Other purposes and advantages of the present disclosure will become more obvious with the following detailed description of the invention, claims, and drawings.

Technical Solution

In accordance with an aspect of the present invention, there is provided a magnetic resonance imaging (MRI) T1 contrast agent composition including a T1 contrast material coated on a surface of a nanoparticle support, wherein the ratio of the thickness of the T1 contrast material coating layer to the diameter of the nanoparticle support is 1:200 to 1:1.

The present inventors have endeavored to develop a contrast agent composition which exerts an excellent T1 MRI contrast effect by effectively inducing spin-lattice relaxation of hydrogen in the water molecule. As a result, the present inventors have found that, in cases where a paramagnetic T1 contrast material is coated on a nanoparticle support having a predetermined diameter such that the paramagnetic T1 contrast material has a predetermined thickness or less, the surface-to-volume ratio of the T1 contrast material increases, and thus the paramagnetic T1 contrast material has a significantly improved T1 magnetic spin relaxation effect (r1, regardless of the molecular size of the contrast material.

According to the present invention, in cases where the T1 contrast material is coated on the surface of the nanoparticle support while the thickness of the T1 contrast material coating layer is adjusted such that the ratio between the diameter of the nanoparticle support and the thickness of the T1 contrast material coating layer is maintained at a predetermined level, the surface-to-volume ratio of the T1 contrast material is maximized, and thus the T1 contrast material can obtain a high T1 contrast effect (about 8.5 mM$^{-1}$s$^{-1}$ at the maximum, and an increase of about 4 times compared with the existing commercialized Teslascan) when compared with existing materials.

As used herein, the term "magnetic resonance imaging (MRI)" refers to a diagnostic technique in which anatomical, physiological, and biochemical information of the human body is obtained through images using the spin relaxation of hydrogen atoms in the magnetic field, thereby performing invasive, real-time imaging of human or animal body organs.

As used herein, the term "T1 contrast agent" refers to a positive contrast agent that lightens a region to be diagnosed, by allowing an image signal of the body region to be relatively higher than that of the surrounding. The T1 contrast agent is associated with T1 relaxation, that is, longitudinal relaxation. The longitudinal relaxation refers to a procedure in which magnetization component Mz in a direction of the Z axis of a spin absorbs the RF energy impact applied from the X-axis, and then is aligned with the Y axis on the X-Y plane to release energy, returning to the original value, and this phenomenon is called "T1 relaxation". The T1 contrast material usable herein includes any material that can generate a T1 signal. More specifically, the T1 contrast material includes a magnetic material, and more specifically, the T1 contrast material is composed of a material containing a paramagnetic material component.

As used herein, the term "coating" refers to binding to a surface of a material, which is an object of coating (modification), without changing basic physical properties of the material. For example, the expression that the T1 contrast material is coated on a surface of a nanoparticle support means that the T1 contrast material directly or indirectly binds to a delocalized area of the surface of the nanoparticle support. Therefore, it would be obvious that the term "coating" used herein does not indicate only the case in which a layer completely blocking a surface of the material, which is an object of coating, is formed. More specifically, the term "coating" used herein means occupying or binding to a surface to such an extent that a surface-to-volume ratio enough to obtain a desired T1 contrast effect can be secured.

According to a specific embodiment of the present invention, the T1 contrast material used herein is metal ion M$^{n+}$ (M is Ti$^{n+}$, V$^{n+}$, Cr$^{n+}$, Mn$^{n+}$, Fe$^{n+}$, Co$^{n+}$, Ni$^{n+}$, Cu$^{n+}$, Ru$^{n+}$ (0<n≤14), or a lanthanide metal), a metal oxide, a metal complex compound, a metal compound, or a multi-component hybrid structure thereof. Specific examples of the lanthanide metal used herein include Eu$^{n+}$, Gd$^{n+}$, Tb$^{n+}$, Dy$^{n+}$, Ho$^{n+}$, Er$^{n+}$, Tm$^{n+}$, Yb$^{n+}$, and Lu$^{n+}$ (0<n≤14), but are not limited thereto.

According to a more specific embodiment of the present invention, the T1 contrast material used herein is metal oxide $M_xO_y$ (M is at least one metal element selected from the group consisting of Ti$^{n+}$, V$^{n+}$, Cr$^{n+}$, Mn$^{n+}$, Fe$^{n+}$, Co$^{n+}$, Ni$^{n+}$, Cu$^{n+}$, Ru$^{n+}$ (0<n≤14), and a lanthanide metal; and 0<x≤16, 0<y≤8). More specifically, the metal oxide is $M_xO_y$ (M=Mn, 0<x≤4, 0<y≤4).

Herein, the metal complex compound used as a T1 contrast material refers to any material that is composed of a central metal and ligands capable of being coordinated on the metal, and especially, a complex compound composed of a metal exhibiting magnetism due to unpaired electrons and coordination ligands. A specific example thereof is $M_xL_y$ (M is at least one element selected from the group consisting of Ti$^{n+}$, V$^{n+}$, Cr$^{n+}$, Mn$^{n+}$, Fe$^{n+}$, CO$^{n+}$, Ni$^{n+}$, Cu$^{n+}$, Ru$^{n+}$ (0<n≤14), and a lanthanide metal; L is at least one ligand capable of being coordinated on the metal; and 0<x≤10, 0<y≤120). The metal complex compound includes, more specifically, a metal chelate, a metal organic framework (MOF), or a coordination polymer.

The metal compound usable as the T1 contrast material includes metal chalcogen (group 16 element) compounds, metal pnicogen (group 15 element) compounds, metal carbon group (group 14) compounds, and metal boron group (group 13) compounds.

According to a specific embodiment of the present invention, specific examples of the metal chalcogen compound usable as a T1 contrast material include $Ma_xA_z$, $Ma_xMb_yA_z$ ($M^a$=at least one element selected from the group consisting of lanthanide elements (Ce, Pr, Nd, Pm, Sm, Gd, Eu, Tb, Dy, Ho, Er, Tm, Yb, and Lu) and transition metal elements (Ti, V, Cr, Mn, Fe, Co, Ni, Cu, and Ru); $M^b$=at least element selected from the group consisting of group 1 metal elements, group 2 metal elements, group 13-15 elements, group 17 elements, transition metal elements, lanthanide elements, and actinide elements; A is at least one selected from the group consisting of O, S, Se, Te, and Po; and 0<x≤16, 0<y≤16, 0<z≤8), and a multi-component hybrid structure thereof, and most preferably, $M^a{}_xO_z$, $M^a{}_xM^b{}_yO_z$ ($M^a$=at least one element selected from the group consisting of lanthanide elements (Ce, Pr, Nd, Pm, Sm, Gd, Eu, Tb, Dy, Ho, Er, Tm, Yb, and Lu), and transition metal elements (Ti, V, Cr, Mn, Fe, Co, Ni, Cu, and Ru); $M^b$=at least one element selected from the group consisting of group 1 metal elements, group 2 metal elements, group 13-15 elements, group 17 elements, transition metal elements, lanthanide elements, and actinide elements; and 0<x≤16, 0<y≤16, 0<z≤8).

Specific examples of the metal pnicogen usable as a T1 contrast material include $M^c{}_xA_z$, $M^c{}_xM^d{}_yA_z$ ($M^c$=at least one element selected from the group consisting of lanthanide elements (Ce, Pr, Nd, Pm, Sm, Gd, Eu, Tb, Dy, Ho, Er, Tm, Yb, and Lu) and transition metal elements (Ti, V, Cr, Mn, Fe, Co, Ni, Cu, and Ru) ; $M^d$=at least one element selected from the group consisting of group 1 metal elements, group 2 metal elements, group 13-14 elements, group 15 elements, group 17 elements, transition metal elements, lanthanide elements, and actinide elements; A is at least one selected from the group consisting of N, P, As, Sb, and Bi; and $0<x\leq24$, $0y\leq24$, $0<z\leq8$).

Specific examples of the metal carbon group compound usable as a T1 contrast material include $M^e_x A_z$ and $M^e_x M^f_y A_z$ ($M^e$=at least one element selected from the group consisting of lanthanide elements (Ce, Pr, Nd, Pm, Sm, Gd, Eu, Tb, Dy, Ho, Er, Tm, Yb, and Lu) and transition metal elements (Ti, V, Cr, Mn, Fe, Co, Ni, Cu, and Ru); $M^f$=at least one element selected from the group consisting of group 1 metal elements, group 2 metal elements, group 13-14 elements, group 15 elements, group 17 elements, transition metal elements, lanthanide elements, and actinide elements; A is at least one selected from the group consisting of C, Si, Ge, Sn, and Pb; and $0<x\leq32$, $0<y\leq32$, $0<z\leq8$).

Specific examples of the metal boron group compound usable as a T1 contrast material include $M^i_x A_z$ and $M^i_x M^j_y A_z$ ($M^i$=at least one element selected from the group consisting of lanthanide elements (Ce, Pr, Nd, Pm, Sm, Gd, Eu, Tb, Dy, Ho, Er, Tm, Yb, and Lu) and transition metal elements (Ti, V, Cr, Mn, Fe, Co, Ni, Cu, and Ru); $M^j$=at least one element selected from the group consisting of group 1 metal elements, group 2 metal elements, group 14-14 elements, group 15 elements, group 17 elements, transition metal elements, lanthanide elements, and actinide elements; A is at least one selected from the group consisting of B, Al, Ga, In, and Tl; and $0<x\leq40$, $0<y\leq40$, $0<z\leq8$).

The metal chelate compound used herein includes a central metal and a chelate ligand capable of binding to the central metal using both of two or more functional groups. Specific examples of the chelate ligand include ethylenediamietetraacetic acid (EDTA), diethylenetriaminepentaacetic acid (DTPA), N-[2-[bis(carboxymethyl)amino]-3-(4-ethoxyphenyl)propyl]-N-[2-[bis(carboxymethyl)amino] ethyl]-L-glycine (EOB-DTPA), N,N-bis[2-[bis(carboxymethyl)amino]ethyl]-L-glutamic acid (DTPA-GLU), N,N-bis[2-[bis(carboxymethyl)amino]ethyl]-L-lysine (DTPA-LYS), N,N-bis[2-[carboxymethyl[(methylcarbamoyl)methyl] amino]ethyl]glycine (DTPA-BMA), 4-carboxy-5,8,11-tris (carboxymethyl)-1-phenyl-2-oxa-5,8,11-triazatridecan-13-oic acid (BOPTA), 1,4,7,10-tetraazacyclododecan-1,4,7,10-tetraacetic acid(DOTA), 1,4,7,10-tetraazacyclododecan-1,4,7-triacetic acid(DO3A), 10-(2-hydroxypropyl)-1,4,7,10-tetraazacyclododecan-1,4,7-triacetic acid (HPDO3A) 2-methyl-1,4,7,10-tetraazacyclododecane-1,4,7,10-tetraacetic acid (MCTA), $(\alpha,\alpha',\alpha'',\alpha''')$-tetramethyl-1,4,7,10-tetraazacyclododecan-1,4,7,10-tetraacetic acid (DOTMA), 3,6,9,15-tetraazabicyclo[9.3.1]pentadeca-1(15),11,13-triene-3,6,9-triacetic acid (PCTA), 4-carboxy-5,8,11-bis (carboxymethyl)-1-phenyl-12-(phenylmethoxy)methyl-8-phosphomethyl-2-oxa-5,8,11-triazatridecan-12-oid acid (BOPTA), N,Ny-phosphonomethylimino-di-2,1-ethanediyl-bis(N-carboxymethyl glycine, N,Ny-phosphonomethyl-imino-di-2,1-ethanediyl-bis(n-phosphonomethylglycine, N,W-(phosphinomethylimino-di-2,1-ethanediyl-bis-(N-(carboxymethyl)glycine, 1,4,7,10-tetraazacyclodecane-1,4,7,10-tetrakis(methylphosphonic acid) (DOTP), 1,4,7,10-tetraazacyclodecane-1,4,7,10-tetrakismethylene (methyl phosphinic acid) (DOTMP), or derivatives thereof, but are not limited thereto.

At least one multi-component hybrid structure of metal ions, metal oxides, metal complex compounds, and metal compounds used herein may be, for a specific example, a compound in which a complex compound ligand is further coordinated on the inorganic compound or a ligand is substituted with a component element of the inorganic compound, but is not limited thereto. $M_2O(CO_3)_2 \cdot H2O$ ($M=Ti^{n+}$, $V^{n+}$, $Cr^{n+}$, $Mn^{n+}$, $Fe^{n+}$, $Co^{n+}$, $Ni^{n+}$, $Cu^{n+}$, $Ru^{n+}$ ($0<n\leq14$) or a lanthanide metal), which is a specific example of the hybrid structure, may be used as a T1 contrast agent of the present invention, and the compound is a multi-component hybrid structure in which two oxygen atoms of $M_2O_3$, which is one of metal oxides, are substituted with the CO3 ligands. In addition, the multi-component hybrid structure usable as a T1 contrast agent is mixed with at least one of ion, a metal, a metal oxide, a metal complex compound, and a metal compound, and thus may be present in various structures and shapes.

As used herein, the term "nanoparticle support" refers to a support material which has a nano-level diameter, and serves as a base on which a T1 contrast material coating layer is formed. As a support material, any material that does not inhibit a contrast effect due to the absence of the magnetic property may be used. Specifically, examples of the support material include inorganic chalcogen compounds, inorganic pnicogen compounds, inorganic carbon group compounds, inorganic boron group compounds, organic polymers, copolymers, ceramic materials, metal complex compounds, and the like.

The support material may have various shapes, such as a sphere shape, a polyhedral shape, a bar shape, and a plate shape. A specific example thereof is a sphere shape. The T1 contrast material is coated on the surface of the support material, and thus the T1 contrast agent has a wide surface area compared with the volume.

According to a specific embodiment of the present invention, the nanoparticle support of the present invention is an inorganic chalcogen $M_xA_y$ nanoparticle support (M is at least one element selected from the group consisting of group 2 elements (Be, Mg, Ca, Sr, Ba), group 13 elements (Al, In, Tl), group 14 elements (Si, Ge, Sn, Pb), group 15 elements (As, Sb, Bi), transition metal elements (Sc, Ti, V, Zn, Y, Zr, Nb, Mo), lanthanide elements (Ce, Pr, Nd, Pm, Sm, Eu, Lu), and actinide elements; A is at least one element selected from the group consisting of O, S, Se, and Te; and $0<x\leq16$, $0<y\leq8$). More specifically, the nanoparticle support is a $SiO_2$ nanoparticle support.

The inorganic pnicogen compound usable as the nanoparticle support of the present invention is, preferably, $M_xA_z$ (M=at least one selected from the group consisting of group 1 elements, group 2 elements, group 13 elements, group 14 elements, group 16 elements, group 17 elements, transition metal elements, lanthanide elements, and actinide elements; A is at least one element selected from the group consisting of N, P, As, Sb, and Bi; and $0<x\leq24$, $0<y\leq8$), or a multi-component hybrid structure thereof, and more preferably $M_xA_z$ (M=at least one elements selected from the group consisting of group 1 elements (Li, Na, K, Rb) , group 2 elements (Be, Mg, Ca, Sr, Ba), group 13 elements (B, Al, In, Tl), group 14 elements (C, Si, Ge, Sn, Pb), group 16 elements (S, Se, Te, Po), group 17 elements (F, Cl, Br, I), transition metal elements (Sc, Ti, V, Zn, Y, Zr, Nb, Mo, Pd, Ag, Cd, W, and Re), lanthanide elements (Ce, Pr, Nd, Pm, Sm, Eu, and Lu), and actinide elements; A is at least one selected from the group consisting of N, P, As, Sb, and Bi; and $0<x\leq24$, $0<y\leq8$), or a multi-component hybrid structure thereof.

The inorganic carbon group compound usable as the nanoparticle support is $M_xA_z$ (M=at least one element selected from the group consisting of group 1 elements, group elements, group 13 elements, group 15-17 elements, transition metal elements, lanthanide elements, and actinide elements; A is at least one selected from the group consisting of C, Si, Ge, Sn, and Pb; and $0<x\leq32$, $0<y\leq8$), or a multi-component structure thereof.

The inorganic boron group compound usable as the nanoparticle support is $M_xA_z$ (M=at least one element selected from the group consisting of group 1 elements, group 2 elements, group 14-17 elements, transition metal elements, lanthanide elements, and actinide elements; A is at least one selected from the group consisting of B, Al, Ga, In, and Tl; and $0<x\leq40$, $0<y\leq8$), or a multi-component structure thereof.

According to a more specific embodiment of the present invention, the organic polymer material or copolymer usable as the support includes any polymer that has hardness. More specific examples thereof include polyesters, polyhydroxyalkanoates (PHAs), poly($\alpha$-hydroxy acid), poly($\beta$-hydroxy acid), poly(3-hydroxybutyrate-co-valerate) (PHBV), poly (3-hydroxyproprionate) (PHP), poly(3-hydroxyhexanoate) (PHH), poly(4-hydroxy acid), poly(4-hydroxybutyrate), poly(4-hydroxy-valerate), poly(4-hydroxyhexanoate), poly (ester amide), polycaprolactones, polylactides, polyglycolides, poly(lactide-co-glycolide) (PLGA), polydioxanones, polyorthoesters, polyanhydrides, poly(glycolic acid-co-trimethylene carbonate), polyphosphoesters, polyphoester urethanes, poly(amino acids), polycyanoacrylates, poly(trimethylene carbonate), poly(imino carbonate), poly (acrylate-co-styrene), pluronic copolymers, polyacrylamides, polyethyleneglycols, poly(tyrosine carbonate), polycarbonates, poly(tyrosine acrylate), polyalkylene oxalates, polyphosphazenes, polyhydroxyalkanoate-polyethylene glycol (PHA-PEG), ethylenevinylalcohol copolymers (EVOH), polyurethanes, polystyrenes, polyesters, polyolefins, polyisobutylenes and ethylene-alpha olefin copolymers, styrene-isobutylene-styrene triblock copolymers, acrylic polymers and copolymers, vinyl halide polymers and copolymers, polyvinyl chloride, polyvinyl ethers, polyvinyl methyl ethers, polyvinylidene halides, polyvinylidene fluorides, polyvinylidene chlorides, polyfluoroalkenes, polyperfluoroalkenes, polyacrylonitriles, polyvinyl ketones, polyvinyl aromatics, polystyrenes, polyvinyl esters, polyvinyl acetates, ethylene-methyl methacrylate copolymers, acrylonitrile-styrene copolymers, poly(acrylonitrile, butadiene, styrene (ABS) resin, ethylene-vinyl acetate copolymers, polyamides, alkyd resins, polyoxymethylenes, polyimides, polyethers, polyacrylates, polymethacrylates, polyacrylic acid-co-maleic acid, poly-L-lysine, polystyrenes, polymethyl methylacrylate copolymers, poly-p-phenylene vinylene (PPV), poly allyl amines, sulfonated polystyrenes, polyvinylsulfate-polyvinylamine copolymers, polydiallylmethyl ammonium chlorides, poly-3,4-ethylenedioxythiophenes (PEDOT), polyacrylamidosulfonic acid (PAMPS), or derivatives or polymers thereof, but are not limited thereto.

The ceramic material usable as the support includes, specifically, inorganic chalcogen maerials, such as inorganic oxides, and includes, for example, titania, zirconia, silica, alumina, aluminate inorganic compounds, silicates inorganic compounds, zeolites, titanate inorganic compounds, ZnO, belemnite inorganic compounds, potassium phosphate inorganic compounds, calcite, apetite inorganic compounds, Sialon (silicon aluminium oxynitride), vanadate inorganic compounds, potassium titanyl phosphate (KTP) inorganic compounds, potassium titanyl Arsenate (KTA) inorganic compounds, borate inorganic compounds, fluoride inorganic compounds, fluorophosphate inorganic compounds, tungstate inorganic compounds, molybdate inorganic compounds, gallate inorganic compounds, selenide inorganic compounds, telluride inorganic compounds. niobate inorganic compounds, tantalate inorganic compounds, cuprite ($Cu_2O$), ceria, bromelite (BeO), a porous material (e.g.: mesoporous crystalline material (MCM)-41, MCM-48, SBA-15, SBA-16, a mesoporous or microporous material), or multi-component hybrid structures thereof, but are not limited thereto.

The nanoparticle support includes, specifically, a metal complex compound. The metal complex compound refers to any material composed of a central metal and ligands capable of being coordinated on the metal, and especially, the metal complex compound usable as the support is a complex compound composed of a central metal not exhibiting magnetism and coordination ligands. Preferably, the ligand includes $M_xL_y$ (M=at least one element selected from the group consisting of group 1 elements, group 2 elements, group 13-17 elements, transition metal elements, lanthanide elements, and actinide elements; L=at least one ligand capable of being coordinated on a metal; and $0<x\leq10$, $0<y\leq120$), or multi-component hybrid structures thereof, but are not limited thereto.

The metal complex compound usable as the nanoparticle support includes, more specifically, organometallic compounds, metal organic frameworks (MOF), or coordination polymers.

According to a more specific embodiment of the present invention, the nanoparticle support used herein is an organic polymer. As used herein, the term "organic polymer" includes any material among polymers having an organic molecule as a monomer, which can serve as a support material of the T1 contrast agent coating layer due to hardness thereof.

According to a more specific embodiment, the organic polymer used herein is a polysaccharide, and most specifically, dextran.

According to a specific embodiment of the present invention, the organic polymer used herein is a protein, and more specifically, selected from the group consisting of aprotinin, lysozyme, and mixtures. The protein has a characteristic three-dimensional shape and volume depending on the kind and molecular weight thereof, and small particles with a size of 2 nm or less can be easily prepared therefrom.

According to a specific embodiment of the present invention, the nanoparticle support used herein does not include lipid.

According to a specific embodiment of the present invention, the ratio of the thickness of the T1 contrast material coating layer to the diameter of the nanoparticle support is 1:100 to 1:2.5.

According to a specific embodiment of the present invention, the ratio of the thickness of the T1 contrast material coating layer to the diameter of the nanoparticle support is 1:60 to 1:3.

According to a specific embodiment of the present invention, the ratio of the thickness of the T1 contrast material coating layer to the diameter of the nanoparticle support is 1:30 to 1:3.

According to a specific embodiment of the present invention, the ratio of the thickness of the T1 contrast material coating layer to the diameter of the nanoparticle support is 1:20 to 1:3.

According to a specific embodiment of the present invention, the ratio of the thickness of the T1 contrast material coating layer to the diameter of the nanoparticle support is 1:20 to 1:5, and more specifically, 1:10 to 1:5.

According to a specific embodiment of the present invention, the thickness of the T1 contrast material coating layer is 0.1 to 5 nm.

More specifically, the thickness of the T1 contrast material coating layer is 0.1 to 3 nm, and more specifically, 0.1 to 2 nm.

According to a specific embodiment of the present invention, the diameter of the nanoparticle support is 50 nm or less, more specifically, 40 nm or less, and more specifically, 2 to 40 nm.

According to a specific embodiment of the present invention, the diameter of the nanoparticle support is 2 to 35 nm, more specifically 2 to 30 nm, still more specifically 2 to 20 nm, still more specifically 2 to 17 nm, and most specifically 2 to 10 nm.

The range of the overall particle size of the T1 contrast agent composition (nanoparticle support particles coated with a T1 contrast material) supposed herein is a very important technical feature to obtain continuous and intermittent MRI images while the T1 contrast agent remains in the blood for a long period of time, as well as a core technical factor that must be taken into consideration to keep an excellent nuclear spin relaxation rate. The present inventors have found the ratio between the optimal thickness of the T1 contrast material coating layer and the diameter of the support, at which the T1 contrast material coated on the nanoparticle support has the maximized surface-to-volume ratio within the range in which the T1 contrast material coating layer has the minimum thickness so as to cause nuclear spin relaxation and the overall particle size so as to serve as a contrast agent.

According to an embodiment of the present invention, it was verified that 25 nm-diameter nanoparticles coated with a 1 nm-thick T1 contrast material ($Mn_3O_4$) showed a T1 magnetic spin relaxation effect, which increased by about 224% compared with the existing Gd chelate-based contrast agent (MAGNEVIS™), about 369% compared with the existing Mn chelate-based contrast agent (TESLAS-CANTh), about 347% compared with $Mn_3O_4$ nanoparticles, and about 2235% compared with MnO nanoparticles.

In addition, the present inventors have observed through nanoparticle supports having various diameters that, in cases where the nanoparticle support has a diameter in the predetermined range, the T1 magnetic spin relaxation effect (r1) effect is maximized within the above range, and have verified that the diameter itself of the nanoparticle support as well as the ratio of the T1 contrast material coating layer to the diameter of the nanoparticle support is an important factor to determine the T1 contrast effect.

According to a specific embodiment of the present invention, the T1 contrast material and the nanoparticle support of the present invention may be bound to each other by an ionic bond, an electrostatic bond, a coordinate bond, a hydrophobic bond, a hydrogen bond, a covalent bond, a hydrophilic bond, or a van der Waals bond, or the T1 contrast material may form a coating layer by growing on the surface of the nanoparticle support.

The contrast agent composition of the present invention may form an additional bond together with a material that stabilizes a dispersion rate of the contrast agent composition and gives biocompatibility to the contrast agent composition. For example, the T1 contrast agent particles of the present invention phase-convert using a water-soluble multi-functional ligand, and thus can be used on an aqueous solution more efficiently.

The T1 MRI contrast agent composition of the present invention is basically used for MRI contrast, but when a material enabling a different type of contrast is bound to the T1 MRI contrast agent, the T1 MRI contrast agent can be used for multi-modal contrast. Here, the different type of contrast material may be directly bound to the contrast agent; may be indirectly bonded to a multi-functional group coated on the contrast agent through a ligand, or may be implemented while being included together with a carrier.

In accordance with another aspect of the present invention, there is provided a method for enhancing a T1 contrast effect of a T1 contrast agent, the method including:

(a) preparing a nanoparticle support; and (b) forming a T1 contrast material coating layer on a surface of the nanoparticle support, wherein the step of preparing the nanoparticle support is performed while the diameter of the nanoparticle support is adjusted to be 2-40 nm.

In accordance with still another aspect of the present invention, there is provided a method for enhancing a T1 contrast effect of a T1 contrast agent, the method including:

(a) preparing a nanoparticle support; and (b) forming a T1 contrast material coating layer on a surface of the nanoparticle support, wherein the step of forming the coating layer is performed while the ratio of the thickness of the T1 contrast material coating layer to the diameter of the nanoparticle support is 1:200 to 1:1.

Since the nanoparticle support, the T1 contrast material, the preparation method thereof, and parameters thereof, which are used herein, have been already described, the descriptions thereof will be omitted to avoid excessive overlapping.

Advantageous Effects

Features and advantages of the present invention are summarized as follows.

(a) The present invention provides a magnetic resonance imaging (MRI) T1 contrast agent composition including a nanoparticle support coated with a T1 contrast material.

(b) The MRI T1 contrast agent composition of the present invention significantly increases the surface-to-volume ratio of the T1 contrast agent material, thereby having an excellent T1 magnetic spin relaxation effect, by coating a paramagnetic T1 contrast material on the nanoparticle support having a predetermined diameter such that the paramagnetic T1 contrast material has a predetermined thickness or less.

(c) The present invention can be favorably used for the image diagnosis with high reliability by providing accurate and clear T1 positive contrast images.

MODE FOR CARRYING OUT THE INVENTION

Hereinafter, the present invention will be described in detail with reference to examples. These examples are only for illustrating the present invention more specifically, and it will be apparent to those skilled in the art that the scope of the present invention is not limited by these examples.

EXAMPLES

Example 1

Synthesis of Silica Nanoparticle Support

Ammonium hydroxide (Sigma-Aldrich, USA) was added to a cyclohexane (Fluka, USA) solution containing IGAPAL CO-520™ (Sigma-Aldrich, USA) to form reverse micelles, and then tetraethoxysilane (Sigma-Aldrich, USA) as a silica precursor was added. The mixture was allowed react at room temperature for 24 hours to synthesize spherical-shaped silica nanoparticles. The thus formed silica nanoparticles were precipitated and separated by centrifugation after the addition of an excessive amount of ethanol. After the separated nanoparticles were re-dispersed in an excessive amount of acetone, extra reactant materials were removed through centrifugation, and finally, the nanoparticles were dispersed in water.

Example 2

Synthesis of 25 nm-sized silica nanoparticle support ($SiO_2$)

A 15% aqueous ammonium hydroxide solution (2.31 mL) was added to a cyclohexane (69.5 g) solution containing IGAPAL CO-520™ (7.45 g) to form reverse micelles, and then tetraethoxysilane (0.25 mL) as a silica precursor was added. The mixture was allowed react at room temperature for 24 hours to synthesize spherical-shaped silica nanoparticles. The silica nanoparticles synthesized by the above method has a size of 25 nm. The thus formed silica nanoparticles were precipitated and separated by centrifugation after the addition of an excessive amount of ethanol. The separated nanoparticles were re-dispersed in an excessive amount of acetone, and extra reactant materials were removed through centrifugation. Finally, the nanoparticles were dispersed in water, and then purified by several filtrations using a filter (ULTRACONEm, Millipore, USA).

Example 3

Size Adjustment of Silica Nanoparticle Support ($SiO_2$)

An aqueous ammonium hydroxide solution (2.31 mL) was added to a cyclohexane (69.5 g) solution containing IGAPAL CO-520™ (7.45 g) to form reverse micelles, and then tetraethoxysilane (0.25 mL) as a silica precursor was added.

Here, 20 nm-, 30 nm-, 40 nm-, and 45 nm-sized silica nanoparticles were, respectively, synthesized by adjusting the concentration of the aqueous ammonium hydroxide solution. The formed silica nanoparticles were precipitated and separated by centrifugation after the addition of an excessive amount of ethanol. The separated nanoparticles were re-dispersed in an excessive amount of acetone, and extra reactant materials were removed through centrifugation. Finally, the nanoparticles were dispersed in water, and then purified by several filtrations using a filter (ULTRACONE™, Millipore, USA).

Example 4

Synthesis of Dextran Nanoparticle Support

Sodium hydroxide (Sigma-Aldrich, USA) and epichlorohydrin (Sigma-Aldrich, USA) were added to an aqueous dextran (Pharmacosmos, Denmark) solution, thereby substituting a hydroxy group of dextran with an epoxide group. Ethylene diamine was added to cross-link dextran chains, thereby synthesizing dextran nanoparticles. The thus synthesized dextran nanoparticles were precipitated and separated by centrifugation after the addition of an excessive amount of ethanol. The separated dextran nanoparticles were re-dispersed in water and then extra reactant materials were removed through a dialysis filter (Spectrum Labs., USA).

Example 5

Size Adjustment of Dextran Nanoparticle Support

Sodium hydroxide (5 N) and epichlorohydrin (6 mL) were added to an aqueous solution (9 mL) containing dextran (1.8 g), thereby substituting a hydroxy group of dextran with an epoxide group. Ethylene diamine (26 mL) was added in a droplet type to cross-link dextran chains, thereby synthesizing dextran nanoparticles. Here, 3 nm-, 5 nm-, 7 nm-, and 12 nm-sized dextran nanoparticles can be synthesized by regulating the rate of ethylene diamine, respectively. The thus synthesized dextran nanoparticles were precipitated and separated by centrifugation after the addition of an excessive amount of ethanol. The separated dextran nanoparticles were re-dispersed in water and then extra reactant materials were removed through a dialysis filter (Spectrum Labs., USA).

Example 6

Preparation of Nano-Sized Protein Support

Protein has a characteristic size and shape depending on the kind and molecular weight thereof. According to the literature (H. P. Erickson et al. *Biol. Proced. Online* 2009, 11, 32.), the size of the protein is proportional to the ⅓ square of the molecular weight of the protein, and specifically, a relationship is provided by $R=0.066M^{1/3}$. Two kinds of proteins (aprotinin and lysozyme) having different molecular weights, to be used as supports, were prepared. Aprotinin (Sigma-Aldrich, USA) and lysozyme (Sigma-Aldrich, USA), which are proteins having molecular weights of 6.7 kDa and 14.3 kDa, respectively, have sizes of 1.2 nm and 1.63 nm, respectively.

Example 7

Synthesis of Nanoparticles including Manganese Oxide Coated on Silica Nanoparticle Support In order to coat a manganese oxide on surfaces of the foregoing synthesized spherical-shaped silica nanoparticles, the following method was conducted. An aqueous colloidal solution, in which silica nanoparticles were dispersed, and $Mn(OAc)_2$ (Sigma-Aldrich, USA), as precursors, were added to an excessive amount of diethylene glycol (Duksan, Korea), followed by a reaction at 90° C. for 12 hours, thereby synthesizing spherical-shaped nanoparticles including a manganese oxide coated on the silica nanoparticle support. In order to remove extra reactant materials, an excessive amount of acetone was added to the synthesized nanoparticles, a centrifugation procedure was repeated several times, and then the nanoparticles was dispersed in water.

Example 8

Surface Modification using Water-Soluble Multi-Functional Group Ligands of Nanoparticles ($SiO_2$@$Mn_3O_4$) including Manganese Oxide Coated on Silica Nanoparticle Support In order to increase stability of the nanoparticles including a manganese oxide coated on silica nanoparticles, synthesized in example 7, in the aqueous solution, a surface modification was performed using dextran, which is one of the aqueous multi-functional group ligands. The surface modification was performed by adding the nanoparticles (10 mg) to distilled water (10 ml) containing dextran (2.25 g) and then performing a reaction at 75° C. for 12 hours. The surface modification was achieved through a metal-ligand coordination bond between manganese of the nanoparticle surface manganese oxide and the hydroxy group of dextran. The nanoparticles upon the completion of the surface modification were purified by removing extra dextran through several filtrations using a filter (UltraCone, Millipore, USA).

Example 9

Synthesis of Nanoparticles including Manganese Oxide Coated on Silica Nanoparticle support In order to coat an iron oxide on the surface of the previously synthesized nanoparticle support (silica, dextran, protein), the following method was performed. $FeCl_3.6H_2O$ (Sigma-Aldrich, USA) and $FeCl_2.4H_2O$ (Sigma-Aldrich, USA) as precursors were added to an aqueous colloidal solution in which nanoparticles were dispersed, followed by stirring. After that, ammonium hydroxide was added, followed by a reaction at room temperature for 10 minutes, thereby synthesizing nanoparticles including an iron oxide coated on the nanoparticle support. Extra iron oxide nanoparticles that were not coated on the support were removed by repeating centrifugation, and then purification was performed using a filter (ULTRACONEm, Millipore, USA) to remove extra reactant materials.

Example 10

Figure 1:
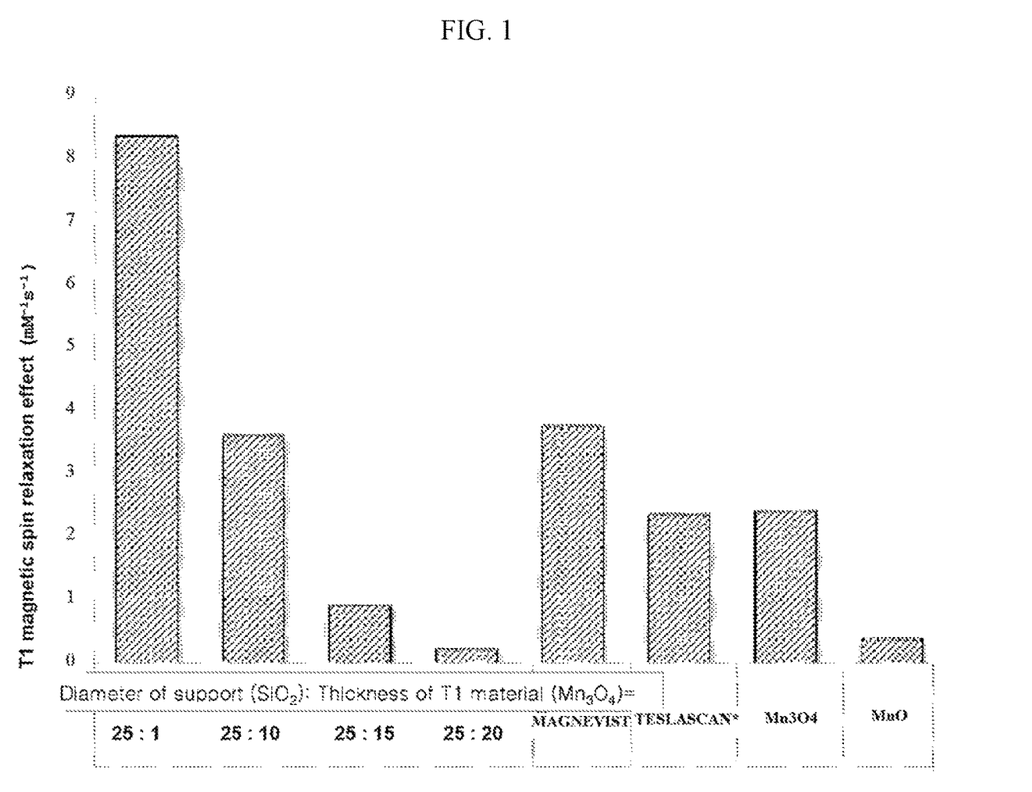
FIG. 1 is a graph showing comparison results of T1 magnetic spin relaxation effects of $SiO_2@Mn_3O_4$ nanoparticles coated with different thicknesses of $Mn_3O_4$ and T1 magnetic spin relaxation effects of existing contrast agents.

Verification on Relationship between Surface-to-Volume Ratio of $Mn_3O_4$ and Magnetic Spin Relaxation Effect after Comparison of Magnetic Spin Relaxation Effect Depending on the Thickness of $Mn_3O_4$; Coating in $SiO_2$@$Mn_3O_4$ Nanoparticles Spherical nanoparticles, which have different thicknesses of $Mn_3O_4$ but the same composition of $SiO_2$@$Mn_3O_4$, were synthesized, and then the T1 magnetic spin relaxation effect ($SiO_2$@$Mn_3O_4$) was measured using a magnetic resonance imaging (MRI) scanner. In order to observe the effect depending on the thickness of $Mn_3O_4$, the other experiment conditions were the same. The specific experiment method was as follows. Each sample was dispersed in water to have concentrations of 0.25 mM, 0.125 mM, and 0.0625 mM (based on manganese), putted in the PCR tube, and then fixed to the support. Subsequently, the support was positioned at the center of the MRI wrist coil (Philips, Netherlands), and then, the Ti relaxation time for each sample was measured using an MRI scanner (1.5 T Philips, Netherlands). After that, in order to calculate an accurate concentration of each sample, the amount of manganese ions was quantified through ICP-AES assay. Based on this, the T1 magnetic spin relaxation effect ((r1)) was obtained. The T1 magnetic spin relaxation effect (r1, $mM^{-1}s^{-1}$) may be obtained by a slope when the reverse ($s^{-1}$) of the T1 relaxation time was plotted with respect to the concentration of manganese ions (mM). The thus obtained values were shown in FIG. 1. The r1 value of the $SiO_2$@$Mn_3O_4$ nanoparticles was shown to be greater as the surface-to-volume ratio is higher since the $Mn_3O_4$ is thin. Actually, the nanoparticles coated with 1 nm-thick $Mn_3O_4$ having the smallest thickness showed a T1 magnetic spin relaxation effect, which increased by about 4285% compared with the nanoparticles coated with 20 nm-thick $Mn_3O_4$. In addition, it was verified that the nanoparticles coated with 1 nm-thick $Mn_3O_4$ showed a T1 magnetic spin relaxation effect, which increased by about 224% compared with the existing metal chelate-based contrast agent (MAGNEVIS™), about 347% compared with $Mn_3O_4$ nanoparticles, and about 2235% as compared with MnO nanoparticles.

Example 11

Figure 2:
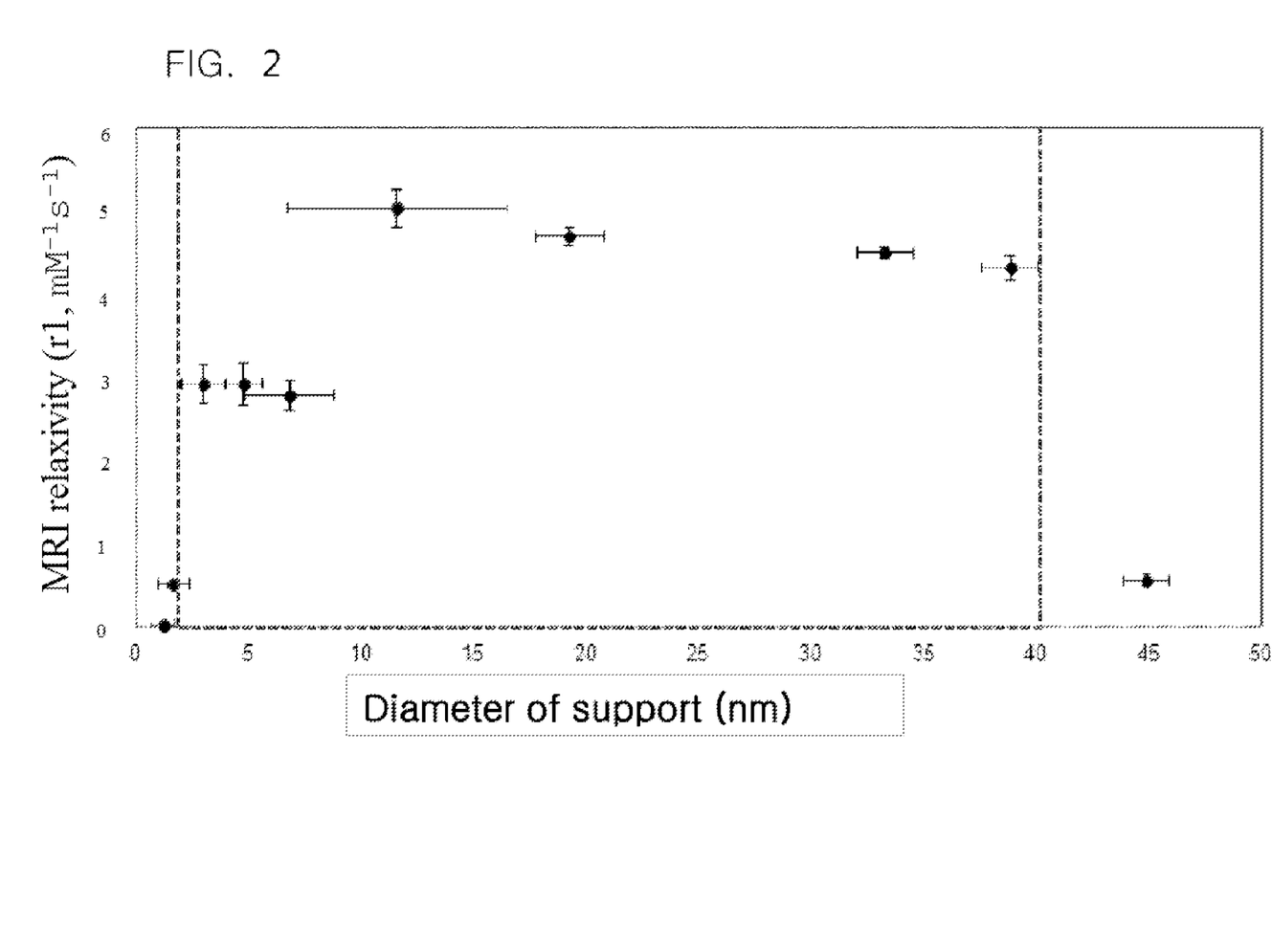
FIG. 2 is a graph showing comparison results of T1 magnetic spin relaxation effects of nanoparticles synthesized by coating an iron oxide on supports having different diameters under the same conditions.

Verification on Relationship between Nanoparticle Support Diameter and Magnetic Spin Relaxation Effect An iron oxide was coated on nanoparticle supports having different sizes under the same conditions, and then the T1 magnetic spin relaxation effects (r1) of nanomaterials were measured using a magnetic resonance imaging (MRI) scanner. The nanoparticle supports used in the present experiment were protein (1.2 nm, 1.63 nm), dextran (3.02 nm, 4.78 nm, 6.83 nm, 11.6 nm), and silica (19.26 nm, 33.29 nm, 38.84 nm, 44.89 nm). A specific experiment method was as follows. Each sample was dispersed in water to have concentrations of 0.25 mM, 0.125 mM, and 0.0625 mM (based on iron), putted in the PCR tube, and then fixed to the support. Subsequently, the support was positioned at the center of the MRI wrist coil (Philips, Netherlands), and then the Ti relaxation time for each sample was measured using an MRI scanner (1.5 T Philips, Netherlands). Based on the measured T1 value and the iron concentration of each sample, the T1 magnetic spin relaxation effect (r1) were obtained. T1 magnetic spin relaxation effect (r1, $mM^{-1}s^{-1}$) may be obtained by a slope when the reverse ($s^{-1}$) of T1 relaxation time was plotted with respect to the concentration of manganese ions (mM). The thus obtained values are shown in FIG. 2. The r1 value was shown to be high for all nanoparticle supports having diameters of 2-40 nm, and significantly low for nanoparticle supports having diameters of 1.2 nm, 1.63 nm, and 44.89 nm.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A magnetic resonance imaging (MRI) method using an iron-based T1 contrast agent for obtaining T1-weighted images in MRI scan, comprising (a) introducing the iron-based T1 contrast agent with a T1 relaxivity coefficient ($r_1$) value ranging from approximately 1 $mM^{-1}s^{-1}$ to 5 $mM^{-1}s^{-1}$ at 1.5 Tesla on an MRI scanner, into a body fluid of a subject, said iron-based T1 contrast agent producing a bright or positive contrast effect compared to water, wherein the MRI iron-based T1 contrast agent consists of
  (i) a non-magnetic nanoparticle support comprising $SiO_2$, a polysaccharide, or a protein wherein a surface of the nanoparticle support comprises surface functional groups, and
  (ii) an iron oxide coating layer having iron oxide bound by coordination bond to the surface functional groups, wherein a ratio of thickness of the iron oxide coating layer to a diameter of the non-magnetic nanoparticle support is to 1:25 to 1:6; the diameter of the non-magnetic nanoparticle support is 2 to 40 nm; and the thickness of the iron oxide coating layer is 0.1 to 1 nm, wherein the iron-based T1 contrast agent shortens T1 relaxation time (spin-lattice relaxation time) to induce a positive contrast on T1-weighted images without inducing a negative contrast associated with a T2 contrast agent; and (b) obtaining T1-weighted images in MRI scan of body parts of the subject.

2. The MRI method of claim 1, further comprising
  (c) using the T1-weighted MRI images obtained from the step (b) as imaging information for medical diagnosis.

3. The MRI method of claim 1, wherein the body parts of the subject are vessels.

4. The MRI method of claim 1, wherein the polysaccharide is a dextran.

5. The MRI method of claim 1, wherein the ratio of the thickness of the iron chelate oxide coating layer to the diameter of the non-magnetic nanoparticle support is 1:25 to 1:10.

6. The MRI method of claim 1, wherein the ratio of the thickness of the iron oxide coating layer to the diameter of the non-magnetic nanoparticle support is 1:25.

7. The MRI method of claim 2, wherein the imaging information is the presence or absence of bleeding in a lesion of the body parts of the subject.

8. The MRI method of claim 7, wherein the body parts of the subject are vessels.

9. The MRI method of claim 1, wherein the ratio of the thickness of the iron oxide coating layer to the diameter of the non-magnetic nanoparticle support is 1:10.

* * * * *